Figure 1:
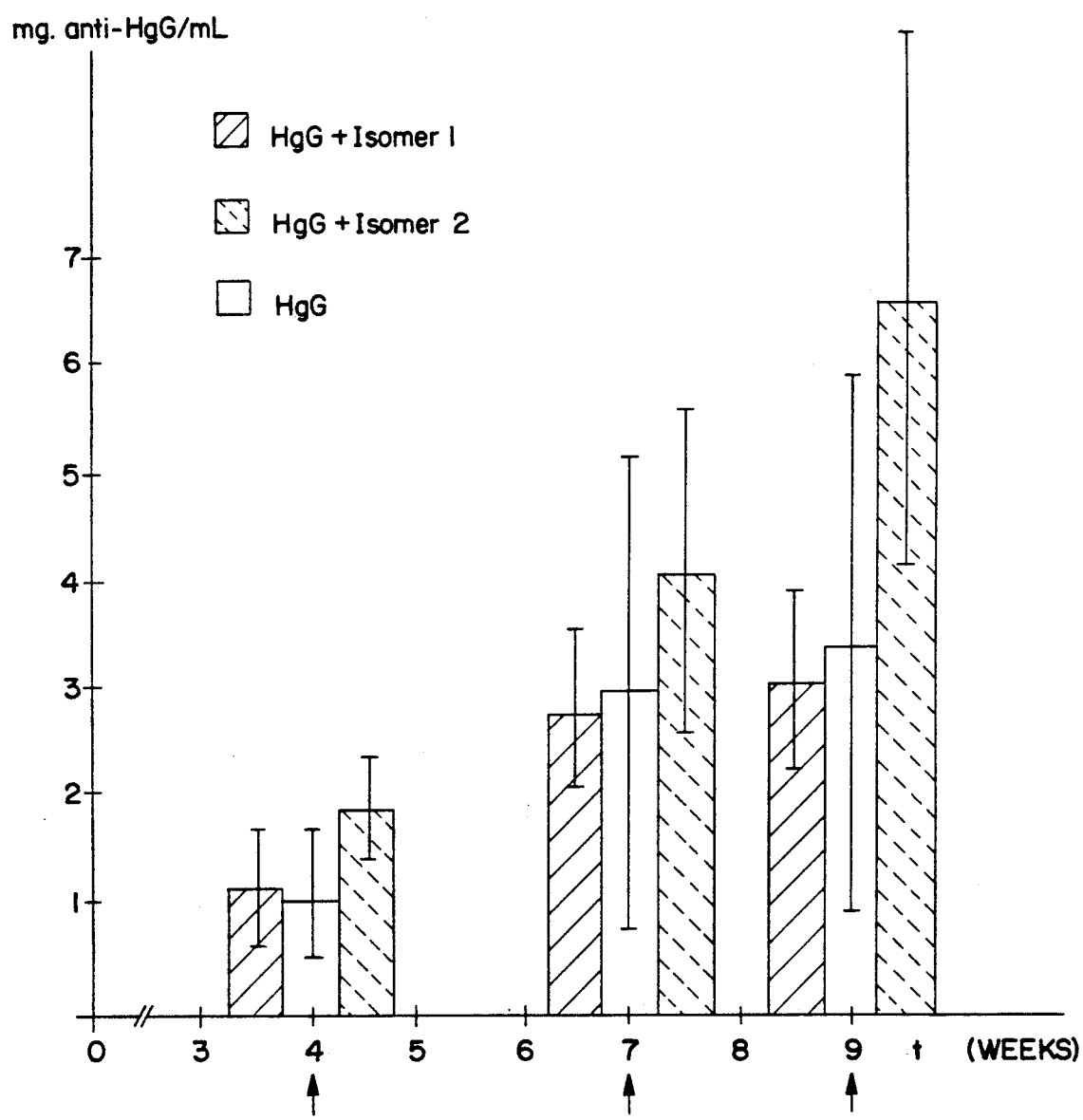

United States Patent [19]

Vranesic et al.

[11] Patent Number: 5,066,642
[45] Date of Patent: Nov. 19, 1991

[54] ADAMANTYL COMPRISING TRIPEPTIDES, DERIVATIVES AND HYDROCHLORIDES THEREOF, THEIR PREPARATION AND USE

[75] Inventors: Branka Vranešić; Jelka Tomašić; Stanislav Smerdel; Darko Kantoci, all of Zagreb, Yugoslavia; Gianni Sava, Trieste, Italy; Ivo Hršak, Zagreb, Yugoslavia

[73] Assignee: Imunoloski Zavod, Yugoslavia

[21] Appl. No.: 477,373

[22] Filed: Feb. 9, 1990

[30] Foreign Application Priority Data

Feb. 9, 1989 [YU] Yugoslavia .............................. 305/89

[51] Int. Cl.$^5$ ..................... A61K 37/00; A61K 37/02; C07K 5/00
[52] U.S. Cl. ...................................... 514/18; 530/331; 514/934
[58] Field of Search ................... 530/331; 514/18, 934

[56] References Cited

U.S. PATENT DOCUMENTS 3,705,141 12/1972 Krimmel et al. ..................... 530/331
4,515,715 5/1985 Flegel et al. ......................... 564/153

FOREIGN PATENT DOCUMENTS 57-099599 6/1982 Japan .

OTHER PUBLICATIONS

CA 111:195410z, Flegel, "Prepn. of N-acetyl-muramyl-L-alanyl-D-isoglutamine-N-(1-adamantyl-)amide", (1989).

*Primary Examiner*—John Doll
*Assistant Examiner*—Carmen Pili Curtis
*Attorney, Agent, or Firm*—Pollock, Vande Sande & Priddy

[57] ABSTRACT

2-Adamantyl- and 1-adamantyl-D/L-glycyl-L-alanyl-D-isoglutamine and their derivatives of the formulae

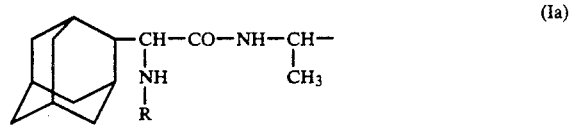

(Ia)

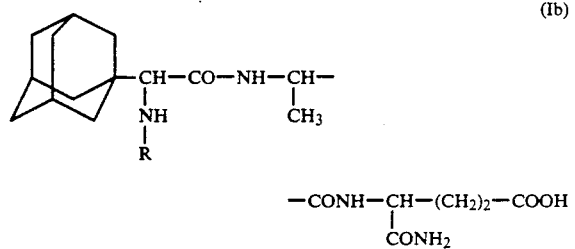

(Ib)

wherein R stands for a hydrogen atom or a MurNAc group, and hydrochlorides thereof, a process for the preparation thereof and their use to obtain pharmaceuticals, which are particularly indicated for the treatment of viral diseases and tumors and/or immunomodulations in humans and animals.

7 Claims, 1 Drawing Sheet

ADAMANTYL COMPRISING TRIPEPTIDES, DERIVATIVES AND HYDROCHLORIDES THEREOF, THEIR PREPARATION AND USE

This invention relates to tripeptides of a novel, characteristic structure, which comprise, in addition to the classical tripeptide form, an adamantane molecule, more particularly to 2-adamantyl- and 1-adamantyl-D/L-glycyl-L-alanyl-D-isoglutamine, and their derivatives, some of them in hydrochloride form, to a process for the preparation thereof and to the use of the new compounds of the invention in pharmaceuticals, which are particularly indicated for the treatment of viral diseases and tumors and/or immunomodulations in humans and animals.

It has been known that the formation of the peptide bond requires the subjection of the amino acid to:

a) the introduction of the so-called protective groups in order to convert it into an N-protected amino acid,
b) the activation of its carboxyl group,
c) the reaction with a C-terminally protected amino acid, a di-, tri- or poly-peptide, and
d) a careful elimination of the protective groups of the resulting di, tri- or poly-peptide by means of specific reactions.

(Houben-Weyl, Methoden der organischem Chemie, 4, Auflage, herausgegeben von Eugen Müller, Synthese von Peptiden I und II, Vol. 15/1 und 15/2, Georg Thieme Verlag, Stuttgart 1974).

It has been known as well that the use of the Woodward's Reagent K (R. B. Woodward, R. A. Olofson, M. Mayer, J. Am. Chem. Soc., 83 (1961) 1010), i.e. by means of 3-unsubstituted isoxazolium salts for the formation of a new peptide bond at very mild conditions results in retaining an unaltered configuration of the optically active centre that takes part in the condensation reaction.

One object of the present invention are new 2-adamantyl- and 1-adamantyl-D/L-glycyl-L-alanyl-D-isoglutamines of the formulae

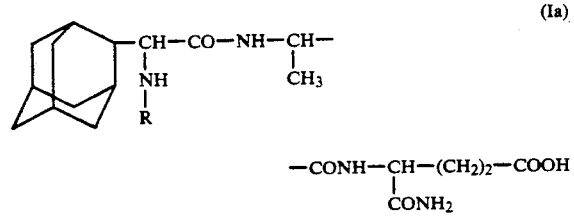

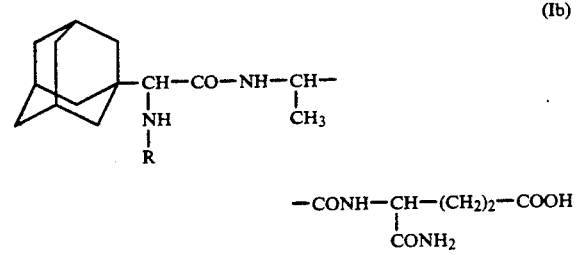

wherein R stands for a hydrogen atom or a MurNAc group, and hydrochlorides thereof.

In the conception of the process for the preparation of the novel tripeptides (1a and 1b) and their hydrochlorides there have been applied per se known methods, e.g. according to the following reaction scheme:

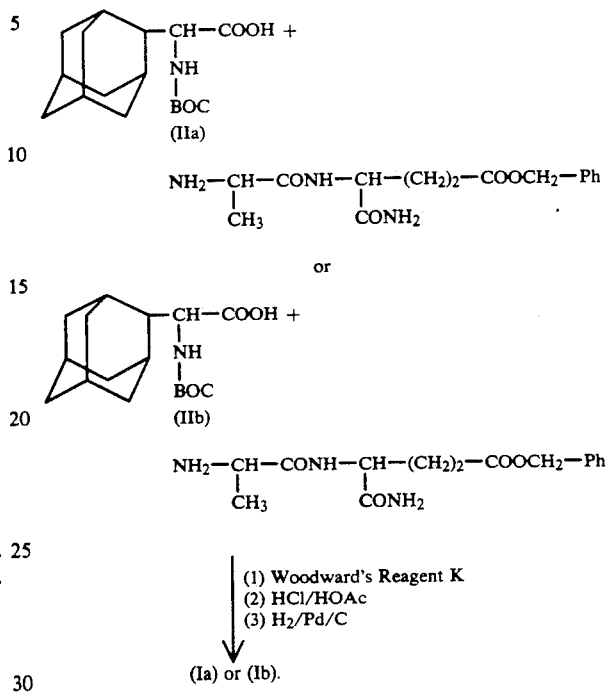

In accordance with the present invention there is performed the condensation of tert-butyloxycarbonyl-2-(or 1-)-adamantyl-D,L-glycine with the benzyl ester of L-alanyl-D-isoglutamine dipeptide in the presence of the Woodward's Reagent K, yielding the completely protected tripeptide. By means of working up with HCl/HOAc and catalytical hydrogenation the deprotected tripeptide is obtained as a mixture of diastereoisomers, which can be successfully resolved by column chromatography on a silicagel column.

The MurNAc derivatives of (Ia) and (Ib), respectively, are obtained by condensation of the benzyl ester of the tripeptide (Ia) or (Ib), wherein R stands for a hydrogen atom, with 4,6-O-benzylidene-N-acetyl-muramic acid, followed by catalytical hydrogenation.

The products (Ia) or (Ib) are characterized by simultaneous antiviral and immunomodulatory properties and possible antitumor activities.

It is a further object of the present invention to provide pharmaceuticals comprising an active, yet physiologically tolerated dose of the novel peptide (Ia) or (Ib) or its hydrochloride and the use thereof in the manufacture of drug formulations for the treatment of viral and tumor diseases and/or for immunomodulation.

Hence the adamantyl compounds of the invention are therapeutically effective in treating cancers. The dosage will depend upon the tumor type to be treated and on the health status in patient subjects. In general, the compounds will be administered at variable doses ranging from 1 to 100 mg/m$^2$ of body surface per day. The optimal dose can be administered in divided doses, while the exact dose will depend on the patient's age, weight and general condition.

The compounds of the invention can be administered by i.v., i.m., s.c. and i.p. routes. The therapeutically active dosage can also be administered on alternate days or for two or more consecutive days followed by two or more days of withdrawal.

The compounds of the invention can also be included into experimental protocols of combination therapy with conventional cytotoxic drugs, such as anthracyclines, cyclophosphamide, blemycine, vinblastine, 5-fluorouracile, cisplatin.

Pharmaceutical compositions containing the compounds of the invention will be prepared according to the standard procedure for human use. Thus for i.v. treatments, infusions or i.m. injections there will be used isotonic solutions and sterile solutions or suspensions in aqueous media prepared immediately before use from lyophilized material containing the active compounds of the present invention.

The invention is illustrated by the following Examples.

EXAMPLE 1 tert-Butyloxycarbonyl-2-adamantyl-D,L-glycine

2-Adamantyl-D,L-glycine (315 mg, 1.5 mmole) was dissolved in a mixture of dioxane-water (2:1, 9 mL) under the addition of 1 N NaOH (5 mL), whereupon di-tert-butyl dicarbonate (361 mg, 1.66 mmole) was added slowly, dropwise, into the solution at ambient temperature. After stirring for 2 hours, a further quantity of di-tert-butyl dicarbonate (100 mg, 0.46 mmole) was added dropwise within 30 minutes. After stirring for 1 hour at room temperature, the dioxane was evaporated and the reaction mixture was acidified to pH 3 by the addition of $KHSO_4$. The reaction mass was then extracted with ethyl acetate (three 15 mL portions), the combined extracts were washed with water (10 mL) and dried over $Na_2SO_4$. After the evaporation of the solvent the product was recrystallized from a mixture of ethyl acetate and n-hexane, yielding 450 mg (97%) of colorless crystals of a mp 168°-170° C. $[\alpha]_D^{20} = -27°$ (c=1, $CHCl_3$), $R_f=0.92$ (in a solvent system n-BuOH; HOAc; $H_2O/12:3:5$).

$^1H$—NMR ($CDCl_3$) δ: 10.71 (s, 1H, COOH), 4.6-4.5 (m, 1H, alpha CH), 2.0-1.6 (m, 15H, Ada), 1.44 (s, 9H, Me—BOC).

$^{13}C$—NMR ($CDCl_3$) δ: 178.05 (COOH), 155.76 (CO BOC), 80.14 (C-tert BOC), 55.8 (alpha CH), 47.29, 38.66, 37.98, 31.66, 29.63, 27.82, 27.59 (Ada), 28.33 (Me—BOC).

Analysis $C_{17}H_{27}NO_4$ (309.406): Calc.: C 65.99; H 8.80; N 4.52%. Found: C 66.22; H 9.08; N 4.27%.

EXAMPLE 2 tert-Butyloxycarbonyl-2-adamantyl-D,L-glycyl-L-alanyl-D-isoglutamine benzyl ester tert-Butyloxycarbonyl-2-adamantyl-D,L-glycine (120 mg, 0.38 mmole) was dissolved in a mixture of acetonitrile and dimethylformamide (2:1:3 mL) under the addition of triethyl amine (50 μL, 36 mg, 0.38 mmole). The reaction mixture was cooled to 0° C. Woodward's Reagent K (97 mg, 0.38 mmole) was added and it was stirred for further 1.5 hours at a temperature of 0°-5° C. Subsequently, L-alanyl-D-isoglutamine benzyl ester obtained from L-alanyl-D-isoglutamine benzyl ester hydrochloride (130 ml, 0.38 mmole) and triethylamine (50 μL, 0.38 mmole) in a mixture of acetonitrile and dimethyl formamide (2:1:1 mL) was added to the reaction mixture. The reaction mixture was kept stirring overnight at ambient temperature. The solvent was then evaporated at reduced pressure and water (20 mL) was added to the residue. After standing for two hours in a freezer, the precipitated product was aspirated and dried. There were obtained 220 mg (95%) of a colorless solid.

After the chromatography of the crude product on a silicagel column with ethyl acetate-light petroleum (2:1) as the solvent system and after the evaporation of the solvents, there were obtained 210 mg (91%) of a colorless solid, which after recrystallization from a mixture of ethyl acetate and n-hexane yielded colorless crystals of the completely protected tripeptide; mp 114°-116° C., $R_f=0.64$ (in ethyl acetate).

$^1H$—NMR ($CDCl_3$) δ: 7.33 (s, 5H, Ph), 5.11 (s, 2H, $CH_2Ph$), 2.6-2.3 (m, 2H, gamma $CH_2$—Gln), 2.3-2.0 (m, 2H, beta $CH_2$—Gln), 2.0-1.5 (m, 15H, Ada), 1.39 (s, 9H, Me—BOC), 1.35 (d, 3H, J=7 Hz, Me—Ala).

$^{13}C$—NMR ($CDCl_3$) δ: 173.87, 172.80, 172.52 (4C, CO), 156.09 (CO—BOC), 135.78, 128.56, 128.27 (Ph), 79.91 (C—BOC), 66.54 ($CH_2Ph$), 55.70 (alpha CH—Ada), 52.43 (alpha CH—Gln), 51.98 (alpha CH—Ala), 49.71, 48.87, 46.45, 38.60, 37.98, 30.53, 29.40, 27.88, 27.71 (Ada), 31.89 (gamma $CH_2$—Gln), 28.39 (beta, $CH_2$—Gln+Me—BOC), 18.23 (Me—Ala).

Analysis $C_{32}H_{46}N_4O_7$: Calc.: C 64.19; H 7.74; N 9.36%. Found: C 64.37; H 7.69; N 9.48%.

EXAMPLE 3

2-Adamantyl-D,L-glycyl-L-alanyl-D-isoglutamine hydrochloride tert-Butyloxycarbonyl-2-adamantyl-D,L-glycyl-L-alanyl-D-isoglutamine benzyl ester (350 mg, 0.6 mmole) was dissolved in acetic acid saturated with hydrogen chloride. After standing for 4 hours at ambient temperature (the reaction was controlled by TLC in a solvent system N-BuOH:HOAc:$H_2O$/12:3:5), the acetic acid was evaporated at reduced pressure and the product was precipitated by the addition of absolute ether. The obtained tert-butyloxycarbonyl-2-adamantyl-D,L-glycyl-L-alanyl-D-isoglutamine benzyl ester hydrochloride was dissolved in 90% aqueous ethanol (20 mL) and hydrogenated overnight under the addition of 10% palladium on carbon (160 mg) at ambient temperature and atmospheric pressure. The catalyst was then separated by centrifugation and the solvent was evaporated. The chromatography of the deprotected tripeptide on a silicagel column with the solvent system $CHCl_3$:i—PrOH:MeOH:$H_2O$:HOAc/20:15:6:4:2) yielded two diastereoisomers in the form of a colorless glassy oil. Prior to the biological testing, each of the diastereoisomers was subjected to chromatography on a Biogel P-2 column with water and lyophilized.

Diastereoisomer 1: 100 mg (224%), $R_f=0.7$ (in the solvent system $CHCl_3$:i—PrOH:MeOH:$H_2O$:-HOAc/20:15:6:4:2).

Mass spectrum: $[M+H]^+ = 409$ $[\alpha]_D^{23} = -56°$ (c=0.5, $H_2O$)

$^1H$—NMR ($D_2O$, dioxane=3.7 ppm) δ: 2.3-2.1 (m, 2H, gamma $CH_2Gln$), 2.1-1.9 (m, 2H, beta $CH_2Gln$), 1.9-1.7 (m, 15H, Ada), 1.22 (d, 3H, J=7.6 Hz, Me—Ala).

—C—NMR ($D_2O$, dioxane=67.4 ppm) δ: 180.76 (COOH), 177.37, 175.40, 170.94 (C=O), 55.53 (alpha CH—Gln+alpha CH—Ada), 50.34 (alpha CH—Ala), 46.45, 38.66, 38.32, 37.70, 31.43, 29.74, 27.88, 27.43 (Ada), 31.72 (gamma, $CH_2$—Gln), 28.16 (beta $CH_2$—Gln), 17.38 (Me—Ala).

Diastereoisomer 2: 180 mg (40.4%), $R_f$=0.6 (in the same solvent system as diastereoisomer 1).

Mass spectrum: $[M+H]^+=409$ $[\alpha]_D^{23}=14°$ (c=0.5, $H_2O$)

$^1$H—NMR ($D_2O$, dioxane=3.7 ppm) δ: 2.3-2.1 (m, 2H, gamma $CH_2$Gln), 2.1-1.56 (m, 17H, beta $CH_2$Gln+Ada), 1.39 (d, 3H, J=7.6 Hz, Me—Ala).

$^{13}$C—NMR ($D_2O$, dioxane=67.4 ppm) δ: 180.59 (COOH), 176.86, 174.66, 170.59 (C=O), 55.08 (alpha CH—Gln), 54.01 (alpha CH—Ada), 50.74 (alpha CH—Ada), 46.50, 38.55, 38.32, 37.70, 33.52, 31.43, 29.35, 27.82, (Ada), 31.83 (gamma $CH_2$—Gln), 28.10 (beta $CH_2$—Gln), 17.10 (Me—Ala).

EXAMPLE 4

N-[2-O-(2-acetamido-2,3-dideoxy-α-D-glycopyranoside-3-yl)-(R)-lactoyl]-2-adamantyl-D,L-glycyl-L-alanyl-D-isoglutamine Benzyl 2-acetamido-4,6-O-benzylidene-3-O-[(R)-1-carboxyethyl]-2-deoxy-α-D-glucopiranoside (141 mg, 0.3 mmole) was dissolved in a mixture of acetontrile and dimethylformamide (2:1, 10 mL) under the addition of triethylamine (30 μg, 0.3 mmole). The reaction mixture was cooled to 0° C., Woodward's Reagent K (76 mg, 0.3 mmole) was added and it was stirred for a further hour. Subsequently, 2-adamantyl-D,L-glycyl-L-alanyl-D-isoglutamine benzyl ester, obtained from 2-adamantyl-D,L-glycyl-L-alanyl-D-isoglutamine benzyl ester hydrochloride (160 mg, 0.3 mmole) and triethylamine (30 μg, 0.3 mmole) in a mixture of acetronitrile and dimethylformamide (2:1:5 mL) was added to the reaction mixture. The reaction mixture was kept stirring overnight at ambient temperature. Upon evaporation of the solvents the product was triturated with water, separated and dried. After the chromatography of the crude product on a silicagel column with the solvent system benzene—ethyl acetate (1:1 ), 170 mg of a colorless solid were obtained.

The obtained N-[2-O-(2-benzyl-2-acetamido-4,6-O-benzylidene-2,3-dideoxy-α-D-glucopyranoside-3-yl)-(R)-lactoyl]-2-adamantyl-D,L-glycyl-L-alanyl-D-isoglutamine benzyl ester (100 mg) was dissolved in a mixture of acetic acid and 96% aqueous ethanol (1:1, 8 mL) and 10% palladium on carbon was added and the reaction mixture was hydrogenated overnight at ambient temperature and atmospheric pressure. Upon separation of the catalyst by centrifugation and evaporation of the solvent, the crude material was purified on a Biogel P-2 column with water, yielding 39.6 mg of a pure N-[2-O-(2-acetamido-2,3-dideoxy-α-D-glucopyranoside-3-yl)-(R)-lactoyl]-2-adamantyl-d,L-glycyl-L-alanyl-D-isoglutamine.

Mass spectrum: $[M+K]^+=722$; $[M+Na]^+=706$ $^1$H—NMR ($D_2O$): 5.07 (d, 1H, $J_{1,2}$=2.64 Hz, H-1), 4.57-4.5 (m, sugar ring protons), 2.37-2.23 (m, 2H, gamma $CH_2$Gln), 2.1-1.7 (m, 17H, beta $CH_2$Gln+Ada), 1.89 (s, 3H, NAcMurNac), 1.3 (d, 3H, J=6.24 Hz, Me—Lact), 1.27 (d, 3H, J=6.35 Hz, Me—Ala).

EXAMPLE 5

Testing of biological activity in vitro 5.1. The testing of the cytotoxic activity of 2-adamantyl-D- and -L-glycyl-L-alanyl-D-isoglutamine hydrochloride was performed by employing the MDCK cell line culture. The investigated parameters were the detecting of the morphological changes and the ability of further multiplication of the cells in a monolayer culture subsequently to a 72 hours contact with both diastereoisomers of 2-adamantyl-D,L-glycyl-L-alanyl-D-isoglutamine hydrochloride. The final concentration of 50 meg in the test volume of the medium did not result in said changes.

5.2. The testing of the antiviral activity with respect to the reduction of the infectivity was performed on H1N1 and H3N2 strains of the influenza A virus. After the simultaneous inoculation of the final concentration of <50 meg of 2-adamantyl-D- and -L-glycyl-L-alanyl-D-isoglutamine hydrochloride into the test volume and the 1 $\log_{10}$ dilution of the virus there was demonstrated a reduction of infectivity of ≧1 $\log_{10}$ with respect to the tested influenza virus strain in the substrate of the MDCK cell line culture.

The in vitro effect (MIC) of the tripeptide of the invention is represented in the following Table.

TABLE 1

| INFLUENZA A subtypes | Symmetrel*** | Tripeptide of the invention | |
|---|---|---|---|
| | | Isomer 1 | Isomer 2 |
| H1N1 | <12.5* | 12.5 | 100 |
| H3N2 | <12.5 | >200?** | 50 |

*Final concentration in mcg
**MIC >200 mcg
***Symmetrel ® (Pliva/Ciba-Geigy), non-proprietary name amantadine The MICs (minimum inhibitory concentrations) of the Isomers 1 and 2 on the growth of two subtypes of the Influenza A virus were studied in MDCK cells ($10^4$ cells/100 μL/well) in comparison with the inhibitory effect of the antiviral compound Symmetrel ®. A reduction of the virus titre (≧1 $\log_{10}$) was detected by measuring the HA activity in samples and controls.

EXAMPLE 6

Testing of biological activity in vitro

Antitumor activity of Isomers 1 and 2

The antitumor activity was examined in CBA mice bearing the MCa mammary carcinoma tumor or in C57BL mice inoculated with B-16 melanoma. The doses tested, 5 and 25 mg/kg bodyweight/day, given i.v. on days 1, 5, 9, 13 after tumor implantation were devoid of severe toxicity.

The results obtained in tumored mice are summarized in the following Tables 2–5 of Examples 6.1–6.4. The following data show the antitumor properties of Isomers 1 and 2. The data reported in Table 2 show that the i.v. treatment on days 1, 5, 9, 13 of mice inoculated with MCa mammary carcinoma on day 0 caused a significant reduction of primary tumor growth. The activity, at the daily dose of 5 mg/kg bodyweight/day, was higher for isomer 2 if compared with isomer 1 and, 24 hours after the last day of the treatment, it consisted of a significant reduction of the volume of the intramuscular tumor by 44%.

The i.v. administration of 25 mg/kg bodyweight/day to mice bearing i.m. MCa mammary carcinoma is also effective on lung metastases formation as evident from Table 3. The spontaneous dissemination of this tumor to the lungs of tumored mice was significantly reduced to 24% of controls by Isomers 2; this compound also caused that 57% of the treated mice were free of macroscopically detectable lung colonies. The effects of Isomer 1 were much less impressive, which indicated that chirality played a certain role in the antitumor and antimetastic effects of these adamantyl derivatives.

Isomer 2 was also more effective than Isomer 1 on the survival time of tumor-bearing mice. The data reported in Table 4 indicated the effectiveness of i.v. treatment with Isomer 2 upon the survival time of mice bearing MCa mammary carcinoma. This effect was consistent with the effectiveness of this compound on the primary tumor growth and on the lung metastases formation and indicated that the reductions of these parameters were therapeutically effective in terms of an increase of the life-span.

The effectiveness of adamantyl tripeptides of the invention on lung metastases formation was also tested in mice bearing melanoma B-16 as shown in Table 5. Following the i.v. administration of 25 mg/body weight/day of both isomers, the dissemination of metastases to the lungs was significantly reduced as shown in Table 5. The administration of Isomer 1 or 2 on day 4 induced the reduction of lung metastases to ⅓ of the number detected in the untreated control groups. Less impressive effect was observed after the treatment on day 7.

These data give unequivocal evidence of the antitumor potentialities of adamantyl tripeptides of the invention in the mammary carcinoma and melanoma B-16 systems.

TABLE 2

Example 6.1: Effects of Isomer 1 and Isomer 2 of the inventive tripeptide on intramuscular tumor growth in mice bearing MCa mammary carcinoma[a]

| Treatment group | Daily dose mg/kg | Primary tumor weight[b] mg ± S.E. | % Inhibition |
|---|---|---|---|
| Controls | — | 1927 ± 219 | — |
| Isomer 1 | 5 | 1387 ± 224 | −28 |
|  | 25 | 1522 ± 182 | −21 |
| Isomer 2 | 5 | 1076 ± 132 | −44 |
|  | 25 | 1559 ± 177 | −19 |

[a]Groups of 7 CBA mice, inoculated i.m. into the calf of the left hind leg with 10[6] viable MCa mammary carcinoma cells on day 0, were given i.v. the test compounds (saline for controls) on days 1, 5, 9, 13.
[b]Evaluated 24 hrs after the last treatment. The tumor growth was estimated by calliper measurements taking tumor density equal to 1 and using the formula: tumor weight = $(\pi/6) \times A^2 \times B$, with A and B as two perpendicular axes (A < B).

TABLE 3

Example 6.2:

| Treatment group[a] | Number of metastatic nodules/mouse | | Animals[b] without metastases % |
|---|---|---|---|
| | mean (min-max) | % Inhibition | |
| Controls | 4.75 (4-6) | — | 0 |
| Isomer 1 | 2.71 (0-5) | −43 | 14.3 |
| Isomer 2 | 1.14 (0-3) | −76 | 57.1 |

[a]Groups of 7 CBA mice, inoculated i.m. into the calf of the left hind leg with 10[6] viable MCa mammory carcinoma cells on day 0, were given i.v. 25 mg/kg of each test compound (saline for controls) on days 1, 5, 9, 13.
Lung metastases evaluation was performed on the freshly removed lung tissue immediately after killing on day 23 by using a low power stereo microscope.
[b]Animals without macroscopically detectable lung metastatic nodules.

TABLE 4

Example 6.3: Effects of Isomer 1 and Isomer 2 of the tripeptide of the invention on the survival time of mice bearing MCa mammory carcinoma[a]

| Treatment group | Daily dose mg/kg | Survival time (days)[b] | |
|---|---|---|---|
| | | mean (min-max) | % Increase |
| Control | — | 22.4 (18-31) | — |
| Isomer 1 | 5 | 24.6 (18-31) | +10 |
|  | 25 | 25.4 (15-40) | +13 |
| Isomer 2 | 5 | 27.4 (18-40) | +22 |

TABLE 4-continued

Example 6.3: Effects of Isomer 1 and Isomer 2 of the tripeptide of the invention on the survival time of mice bearing MCa mammory carcinoma[a]

| Treatment group | Daily dose mg/kg | Survival time (days)[b] | |
|---|---|---|---|
| | | mean (min-max) | % Increase |
|  | 25 | 29.7 (18-40) | +32 |

[a]Groups of 7 CBA mice, inoculated i.m. into the calf of the left hind leg with 10[6] viable MCa mammary carcinoma cells on day 0, were given i.v. the test compounds (saline for controls) on days 1, 5, 9, 13.
[b]Survival time was recorded as the number of days of survival of each mouse from the tumor implantation.

TABLE 5

Example 6.4: Effects of Isomer 1 and Isomer 2 of the inventive tripeptide on lung metastases development in mice bearing melanoma B-16[a]

| Treatment group | Day | Number of metastatic nodules/mouse | | Animals without metastases % |
|---|---|---|---|---|
| | | mean (min-max) | % inhibition | |
| Controls | +4 | 3.14 (0-6) | — | 14 |
| Isomer 1 | +4 | 1.0 (0-2) | −68 | 37 |
| Isomer 2 | +4 | 0.97 (0-2) | −69 | 37 |
| Controls | +7 | 2.64 (0-7) | — | 25 |
| Isomer 1 | +7 | 0.64 (0-1) | −76 | 37 |
| Isomer 2 | +7 | 1.38 (0-4) | −48 | 28 |

[a]Groups of 8 C57BL/6 mice (5-6 months old), inoculated i.v. with 10[5] melanoma B-16 cells on day 0, were given i.v. 25 mg/kg of each test compound (saline for controls) on days 4 or 7.
Macroscopically detectable lung metastases were counted on day 30.

EXAMPLE 7

Immunoadjuvant activity of Isomer 1 and Isomer 2

The immunostimulating property of Isomer 1 and Isomer 2 of 2-adamantyl-D,L-glycyl-L-analyl-D-isoglutamine was tested in rabbits immunized with human gamma globulin (HgG).

New Zealand rabbits (five per group) were immunized s.c. with 0.5 mg of HgG in incomplete Freund's adjuvant. Isomer 1/Isomer 2 (0.3 mg) was administered i.v. in phosphate buffered saline (PBS) three days after immunogen. The formation of anti-HgG antibodies was followed by a solid phase radioimmunoassay method to provide a quantitative measure of anti-HgG antibodies in rabbit sera. Serum antibody content (mg/mL) was determined by parallel line bioassay method, using >Sigma< antihuman IgG (whole molecule) as a standard.

Antibody formation against HgG was significantly enhanced in animals treated with Isomer 2 in comparison to the antibody levels in control groups of animals immunized with HgG in incomplete Freund's adjuvant.

The enclosed FIG. 1 shows the serum antibody responce against HgG following 4 inoculations on days 0, 21, 42 and 56. The bleeding is indicated by arrows on the abscissa axis.

What is claimed is:

1. A compound selected from the group consisting of 2-adamantyl- and 1-adamantyl-D/L-glycyl-L-alanyl-D-isoglutamine and their derivatives of the formulae

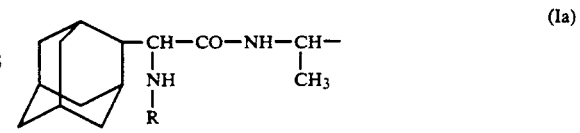

(Ia)

-continued

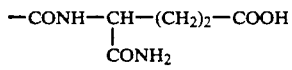

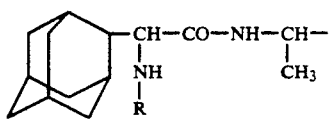

(Ib)

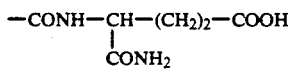

wherein R stands for a hydrogen atom or a MurNAc group, and hydrochlorides thereof.

2. Antiviral composition comprising a compound of claim 1 in a pharmaceutically active yet physiologically tolerated dose of 1-100 mg/m² of body surface per day.

3. Immunomodulatory composition comprising a compound of claim 1 in a pharmaceutically active yet physiologically tolerated dose of 1-100 mg/m² of body surface per day.

4. The compound of claim 1 represented by formula (Ia) or its hydrochloride.

5. The compound of claim 1 represented by formula (Ib) or its hydrochloride.

6. A method of treating influenza viral diseases in humans and animals, which comprises administering an effective amount of 1 to 100 mg/m² of body surface per day of a substance of the formula (Ia) or (Ib) or hydrochlorides thereof as claimed in claim 1, or a composition containing same as an active ingredient.

7. A method of stimulating immune system in humans and animals, which comprises administering an effective amount of 1-100 mg/m² of body surface per day of a substance of the formula (Ia) or (Ib) or hydrochlorides thereof as claimed in claim 1, or a composition containing same as an active ingredient.

* * * * *